United States Patent [19]
Storz

[11] 4,060,086
[45] Nov. 29, 1977

[54] ENDOSCOPE WITH AN OPERATING DEVICE

[76] Inventor: Karl Storz, Auf dem Schildrain 39, 7200 Tuttlingen, Germany

[21] Appl. No.: 689,560

[22] Filed: May 24, 1976

[51] Int. Cl.² .............................................. A61B 17/32
[52] U.S. Cl. ................................................. 128/303.15
[58] Field of Search ...................... 128/303.13–303.18, 128/407–409

[56] References Cited

U.S. PATENT DOCUMENTS

| | | | |
|---|---|---|---|
| 1,713,970 | 5/1929 | Lowry et al. | 128/303.14 |
| 1,717,480 | 6/1929 | Wappler | 128/303.18 |
| 2,018,335 | 10/1935 | Wappler | 128/303.15 |
| 2,102,270 | 12/1937 | Hyams | 128/303.17 |
| 3,990,456 | 11/1976 | Iglesias | 128/303.15 |

FOREIGN PATENT DOCUMENTS

| | | | |
|---|---|---|---|
| 1,020,980 | 2/1953 | France | 128/303.14 |

*Primary Examiner*—Robert W. Michell
*Assistant Examiner*—Lee S. Cohen
*Attorney, Agent, or Firm*—Eugene M. Eckelman

[57] ABSTRACT

The distal insulated end of an endoscope shaft has an inner layer made from a material having a higher heat resistance than the material in the insulated end. Such heat resistant layer preferably contains a ceramic material and is constructed as an inner ring which is inserted and cemented into a correspondingly sized inner groove in the insulating material.

4 Claims, 2 Drawing Figures

ENDOSCOPE WITH AN OPERATING DEVICE

BACKGROUND OF THE INVENTION

The invention relates to an endoscope having a movable electrode supplied with high frequency current at the distal insulated end of the endoscope shaft.

Endoscope of this type are already known by means of which tissue in the vesica or on the cervic vesicae is removed by an electrode which is supplied with high frequency current and which is generally constructed in the form of a wire loop. In such transurethral operations, the tissue and the like is cut at the insulated shaft edge by means of the said electrode. It has been found in practice that when using the said insulating materials, it is impossible to prevent melting of the cutting shaft edge due to sparking on the loop-like electrode. As a result, notches and cup-shaped indentations are formed which can damage the mucosa. In addition, melting of the shaft edge gradually reduces the length of the shaft so that the loop-like electrode does not cut as well after prolonged use. However, the said known materials have the advantage that they do not break because they have a limited elasticity.

The problem of the present invention is to so improve the endoscope of the type indicated hereinbefore that the formation of notches and premature wear due to sparking on the electrode can no longer occur.

SUMMARY OF THE INVENTION

According to the invention, this problem is solved in that the insulated end of the endoscope shaft is provided with a layer of material having a higher heat resistance than the insulating material.

In this connection it is particularly advantageous for the heat resistant layer to contain a ceramic material, this material in fact has the further advantage of being a very good insulating material, so that the insulating material is also protected from the local high temperatures of spark formation through the fact that the heat conduction through the heat resistant layer is only small.

As a further development of the invention, the layer of heat resistant material is in the form of a ring which can be inserted in the insulated end of the endoscope shaft.

As a result, the outer layer is formed from the above-indicated fracture-proof and known insulating material such as Teflon or Epoxy resin, whereas the inner layer forming the cutting edge comprises the heat resistant ceramic material or the like. As a result of this outer layer the ceramic material is protected from fracture, while the inserted ring protects the heat-sensitive insulating material from thermal action.

It is hereby advantageous for the heat resisnant ring to be arranged in a slot of the insulated end and dimensioned in such a way that the ring, the insulated end outside the slot, and the endoscope shaft have the same internal diameter when assembled. In this way the internal diameters of the different parts of the object of the invention pass into one another with apparently the same wall thickness. Thus the passage for the said electrode or other parts, e.g. a washing device, is not impaired.

Further advantages and details of the invention can be gathered from the following description of an embodiment taken with reference to the drawings.

BRIEF DESCRIPTION OF THE DRAWINGS

FIG. 1 shows the endoscope with an endoscope shaft 10, a viewing tube 11 inserted therein, having an eyepiece 12 and an objective lens 13. A loop carrier 14 connected with the appropriate guide block 15 is also arranged in shaft 10.

Figure 1:
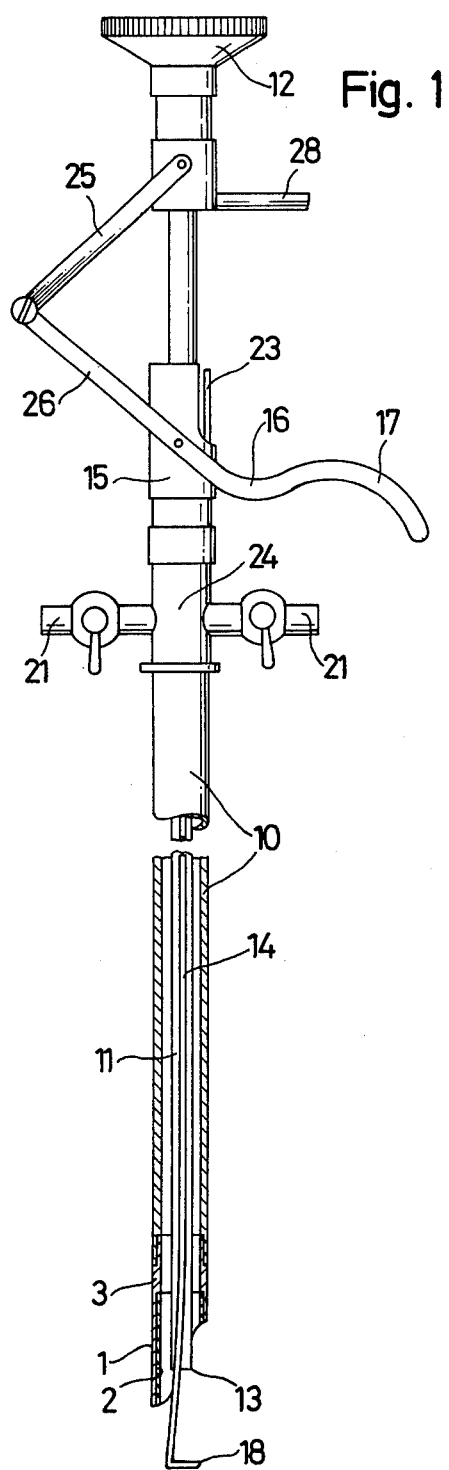
FIG. 1 is a shortened and partly cut-away side view of the invention.

The viewing tube 11 is connected in non-displaceable but interchangeable manner with the endoscope shaft 10, and a considerable proportion of its length projects above the top portion 24 of endoscope shaft 10. At the upper end viewing tube 11 is articulated a lever 25, whose free end is connected in articulated and scissor-like manner with an arm 26 of a hand lever 16, articulated to the guide block 15 and constructed as a handle 17. On operating hand lever 16 relative to an attachment 28 on the eyepiece, the guide block 5 is moved in the longitudinal direction of the viewing tube, which is passed through the guide block.

The loop carrier 14 comprises two parallel tubular rods, not shown in FIG. 1, interconnected at their distal ends by wire loops 18.

The remaining space within the endoscope shaft 10 can also serve as a washing agent channel.

The top portion 24 of the endoscope shaft has on pipe connection with a tap 21 for the supply and another pipe connection with a tap 21 for the discharge of the washing agent.

Loop 18 comprises a flat wire, whose narrow sides form cutting edges. The thickness of this flat wire can be between about 0.12 and 0.15 mm and its width 0.6 to 0.8mm. FIG. 1 shows the wire loop 18 in a side view of the wide side.

Current conductors are arranged in the tubular rods of the loop carrier 14 and carry a high frequency current to the wire loop 18 at the distal end of the endoscope. For connection purposes a plug 23 is provided on the guide block 15.

The hitherto described endoscope requires no further explanation because it forms part of the prior art. It is also know for the distal end 1 of the endoscope shaft 10 to comprise an insulating material such as Teflon or Epoxy resin. According to the invention this insulated end 1 is provided with an inner tubular layer 2, FIG. 2, made from a material which has a higher heat resistance than the insulating material. This heat resistant layer 2 preferably contains a ceramic material and is constructed as an inner tube which is inserted and cemented into a corresponding hollowedout groove 6 of insulating material 1. It is hereby particularly preferred for tube 2, insulating sleeve 1, and endoscope 10, to have the same small internal diameter so that there is a smooth passage internally. Endoscope shaft 10 also has a corresponding internal hollowed-out groove 4, for receiving a correspondingly stepped portion of the insulated end 1, whereby dimensioning is such that externally there is a smooth continuous endoscope shaft up to the distal end of the insulating portion 1. For strength reasons between the end of the inserted ceramic sleeve 2 and the groove 4 of insulating portion 1, a space is left with a adaptor 3 of insulating end 1, which can have the full wall thickness of endoscope shaft 10.

Figure 2:
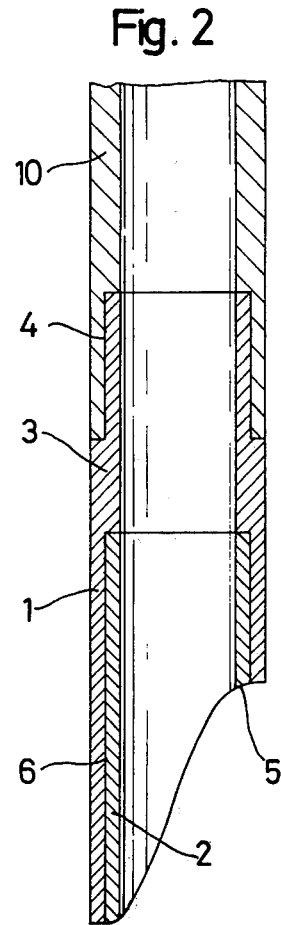
FIG. 2 is an enlarged cut-away view of the distal end of the endoscope shaft of FIG. 1.

The embodiment of FIG. 2 is preferred because as a result two different insulating materials 1 and 2 are formed for the distal end. The outer layer 1 has the advantage that it comprises the said fracture-proof material, while the inner layer has the high heat resistant ceramic material. Thus, the outer layer protects the ceramic material from breakage and the inner layer 2 prevents wear due to sparking on loop 18. As this sparking always occurs on the inner cutting edge 5, outer layer 1 is also protected from excessive heat stressing, particularly as ceramic material is a relatively poor thermal conductor. Thus, heat action does not cause wear to the cutting inner edge 5 and as a result it has a long service life.

Having thus described my invention, I claim:

1. An endoscope comprising a tubular shaft, an electrode in said shaft arranged to be supplied with high frequency current, a distal end on said shaft terminating in an outer tubular insulated portion, said distal end also including an inner tubular layer of material having a higher heat resistance than said insulated portion provided on the interior of said outer tubular insulated portion said inner tubular layer terminating in an end edge, and means for moving aid electrode longitudinally in said shaft whereby said electrode is operable with said end edge upon movement thereof to perform operations.

2. The endoscope of claim 1 wherein said inner tubular layer comprises a ceramic material.

3. The endscope of claim 1 wherein said inner tubular layer comprising a ring-like structure to said outer tubular insulated portion.

4. The endoscope of claim 1 wherein said outer tubular insulated portion has a grooved end and said tubular shaft has an inner groove receiving said grooved end of said outer tubular insulated portion to provide uniform diameter inner and outer surfaces on said shaft at the juncture of said shaft and outer tubular insulated portion, said inner tubular layer having a groove end and said outer tubular insulated portion having an inner groove at the terminal end thereof receiving said grooved end of said inner tubular layer to provide unfirom diameter inner and outer surfaces on said shaft at the juncture of said outer tubular insulated portion and said inner tubular layer.

* * * * *